United States Patent
Kawamura et al.

(10) Patent No.: US 8,043,822 B2
(45) Date of Patent: Oct. 25, 2011

(54) METHOD OF IMMUNOASSAYING A COMPONENT TO BE MEASURED

(75) Inventors: Mizuho Kawamura, Shizuoka (JP); Akihito Tomita, Sunto-gun (JP)

(73) Assignee: Kyowa Medex Co., Ltd., Tokyo (JP)

( * ) Notice: Subject to any disclaimer, the term of this patent is extended or adjusted under 35 U.S.C. 154(b) by 81 days.

(21) Appl. No.: 12/447,311

(22) PCT Filed: Nov. 1, 2007

(86) PCT No.: PCT/JP2007/071344
§ 371 (c)(1),
(2), (4) Date: Jun. 26, 2009

(87) PCT Pub. No.: WO2008/053973
PCT Pub. Date: May 8, 2008

(65) Prior Publication Data
US 2010/0068738 A1    Mar. 18, 2010

(30) Foreign Application Priority Data

Nov. 2, 2006   (JP) .................................. 2006-299498

(51) Int. Cl.
*G01N 33/53*   (2006.01)
(52) U.S. Cl. ......................................... 435/7.1; 436/518
(58) Field of Classification Search .................. None
See application file for complete search history.

(56) References Cited

U.S. PATENT DOCUMENTS

| | | | | |
|---|---|---|---|---|
| 5,952,009 | A * | 9/1999 | Neurath et al. | 424/535 |
| 6,030,845 | A | 2/2000 | Yamao et al. | |
| 6,084,059 | A * | 7/2000 | Matsushita et al. | 528/414 |
| 6,143,510 | A | 11/2000 | Hoshino et al. | |
| 6,180,102 | B1 * | 1/2001 | Hanai et al. | 424/152.1 |
| 6,410,677 | B1 * | 6/2002 | Enoki et al. | 528/170 |
| 6,855,562 | B1 | 2/2005 | Yamao et al. | |
| 7,326,579 | B2 | 2/2008 | Yamao et al. | |
| 7,338,809 | B2 * | 3/2008 | Yokoi | 436/176 |
| 2002/0031791 | A1 | 3/2002 | Uchida et al. | |
| 2002/0076743 | A1 * | 6/2002 | Sakai et al. | 435/34 |
| 2003/0224534 | A1 | 12/2003 | Kawate | |

FOREIGN PATENT DOCUMENTS

| | | |
|---|---|---|
| JP | 04-194664 | 7/1992 |
| JP | 06-265554 | 9/1994 |
| JP | 10-048214 | 2/1998 |
| JP | 10-332697 | 12/1998 |
| JP | 2002-107365 | 4/2002 |
| JP | 2004-045395 | 2/2004 |
| JP | 2006-038823 | 2/2006 |
| JP | 2006-234831 | 9/2006 |
| JP | 2007-225603 | 9/2007 |
| WO | 96/04558 | 2/1996 |
| WO | 99/24833 | 5/1999 |
| WO | 02/073203 | 9/2002 |
| WO | 02/090930 | 11/2002 |

OTHER PUBLICATIONS

Halminen, et al., "Expression of MxA Protein in Blood Lymphocytes Discriminates between Viral and Bacterial Infections in Febrile Children", Pediatric Research, vol. 41, No. 5 (1997) 647-50.
Towbin, et al., "A Whole Blood Immunoassay for the Interferon-Inducible Human MxProtein", Journal of Interferon Research, vol. 12, No. 2 (1992) 67-74.
Viedma, et al., "A New Automated Turbidimetric Immunoassay for Quantifying α1-Antitrypsin in Serum", Clinical Chemistry, vol. 32, No. 6 (1986) 1020-22.

* cited by examiner

*Primary Examiner* — Jacob Cheu
(74) *Attorney, Agent, or Firm* — Fitzpatrick, Cella, Harper & Scinto

(57) ABSTRACT

A method of immunoassaying a component to be measured in a sample containing hemoglobin, which comprises reacting a component to be measured in a sample containing hemoglobin with an antibody capable of binding to the component in the presence of a bile acid derivative different from a bile acid derivative that is inherently contained in the sample; a method of suppressing an interference of hemoglobin in immunoassaying a component to be measured in a sample containing hemoglobin, which comprises reacting a component to be measured in a sample containing hemoglobin with an antibody capable of binding to the component in the presence of a bile acid derivative different from a bile acid derivative that is inherently contained in the sample; a reagent of immunoassay of a component to be measured in a sample containing hemoglobin, which comprises a bile acid derivative, are described.

11 Claims, No Drawings

METHOD OF IMMUNOASSAYING A COMPONENT TO BE MEASURED

TECHNICAL FIELD

The present invention relates to a method of immunoassaying a component to be measured in a sample containing hemoglobin, a reagent of immunoassay, and a method of suppressing an interference of hemoglobin in a method of immunoassaying.

BACKGROUND ART

In a method of immunoassaying a component to be measured in blood that exists outside blood cells such as red and white blood cells, serum or plasma prepared by removing blood cells from whole blood is used as a sample. However, since removal of blood cells requires special equipments such as a centrifuge and is troublesome, methods of measurement using whole blood as a sample have been proposed (see Patent Document 1). When whole blood is used as a sample, it is problematic that a measurement is affected by blood cell components such as hemoglobin or blood cell membrane components contaminated in the sample through hemolysis. These components affect the optical detection system, inhibit immunoreactions, and adsorb the substance to be measured. There are reports of methods of immunoassaying using whole blood as a sample, not accompanied by hemolysis to avoid such problems (see Patent Documents 2, 3, 4, and 5).

When measuring components in blood cell such as intracellular proteins, blood cells must be lysed; therefore, the above-described methods which do not accompany hemolysis cannot be used. In such cases, methods which comprise separation of the blood cells of interest by flow cytometry followed by lysis of the isolated cells and measurement of the desired component in blood cell are used, but these methods require special equipments for flow cytometry and are troublesome.

On the other hand, as an example of convenient methods for measuring intracellular proteins, a method of immunoassaying MxA protein using as a sample for measurement, lysates of blood cells in whole blood prepared using a surfactant, has been reported (Non-patent Documents 1 and 2).

[Patent Document 1] Japanese Patent Application Kokai Publication No. (JP-A) H10-48214 (unexamined, published Japanese patent application)
[Patent Document 2] JP-A (Kokai) H06-265554
[Patent Document 3] WO 96/04558
[Patent Document 4] WO 02/73203
[Patent Document 5] JP-A (Kokai) 2004-45395
[Non-patent Document 1] Journal of Interferon Research, (USA), 1992, Vol. 12, No. 2, p. 67-74
[Non-patent Document 2] Pediatric Research, (USA), 1997, Vol. 41, No. 5, p. 647-650

DISCLOSURE OF THE INVENTION

Problems to be Solved by the Invention

An objective of the present invention is to provide a method and a reagent of immunoassaying a component to be measured in a sample containing hemoglobin to suppress an interference of hemoglobin, and a method of suppressing an interference of hemoglobin in a method of immunoassaying a component to be measured in a sample containing hemoglobin.

Means for Solving the Problems

The present inventors found that in a method of immunoassaying a component to be measured in a sample, the component can be accurately measured by reacting the component with an antibody capable of binding to the component in the presence of a bile acid derivative different from a bile acid derivative that is inherently contained in the sample, and thereby completed the present invention. More specifically, the present invention relates to [1] to [24] below.

[1] A method of immunoassaying a component to be measured in a sample containing hemoglobin, which comprises reacting a component to be measured with an antibody capable of binding to the component in the presence of a bile acid derivative different from a bile acid derivative that is inherently contained in the sample.

[2] The method according to [1], which comprises reacting a component to be measured in a sample containing hemoglobin with an antibody capable of binding to the component, further in the presence of a polyoxyethylene nonionic surfactant.

[3] The method according to [1] or [2], wherein the method of immunoassay is a sandwich method or a competition method.

[4] The method according to [1] or [2], wherein reacting the component with an antibody capable of binding to the component is:
(1) reacting the component with a first antibody capable of binding to the component and a labeled second antibody capable of binding to the component,
(2) reacting the component with a labeled competitive substance and an antibody capable of binding to both of the component and the competitive substance, or
(3) reacting the component with a competitive substance and a labeled antibody capable of binding to both of the component and the competitive substance.

[5] The method according to any one of [1] to [4], wherein the bile acid derivative different from a bile acid derivative that is inherently contained in the sample is a bile acid derivative having amphoteric surfactant function.

[6] The method of any one of [1] to [4], wherein the bile acid derivative different from a bile acid derivative that is inherently contained in the sample is a bile acid derivative having nonionic surfactant function.

[7] The method of [5], wherein the bile acid derivative having amphoteric surfactant function is 3-[(3-cholamidopropyl)dimethylammonio]propanesulfonate (hereinafter, abbreviated as CHAPS) or 3-[(3-cholamidopropyl)dimethylammonio]-2-hydroxypropanesulfonate (hereinafter, abbreviated as CHAPSO).

[8] The method according to [6], wherein the bile acid derivative having nonionic surfactant function is N,N-bis(3-D-gluconamidopropyl)cholamide (hereinafter abbreviated as BIGCHAP) or N,N-bis(3-D-gluconamidopropyl)deoxycholamide (hereinafter abbreviated as deoxy-BIGCHAP).

[9] The method according to any one of [2] to [8], wherein the polyoxyethylene nonionic surfactant is polyoxyethylene alkylphenyl ether.

[10] The method according to any one of [1] to [9], wherein the sample is whole blood.

[11] The method according to any one of [1] to [10], wherein the component to be measured is MxA protein.

[12] A reagent of immunoassay of a component to be measured in a sample containing hemoglobin, which comprises a bile acid derivative and a member selected from the group consisting of (1) to (3) below:

(1) a first antibody capable of binding to the component and a labeled second antibody capable of binding to the component;

(2) a labeled competitive substance and an antibody capable of binding to both of the component and the competitive substance; and (3) a competitive substance and a labeled antibody capable of binding to both of the component and the competitive substance.

[13] The reagent according to [12], which further comprises a polyoxyethylene nonionic surfactant.

[14] The reagent according to [12] or [13], wherein the bile acid derivative is a bile acid derivative having amphoteric surfactant function.

[15] The reagent according to [12] or [13], wherein the bile acid derivative is a bile acid derivative having nonionic surfactant function.

[16] The reagent according to [14], wherein the bile acid derivative having amphoteric surfactant function is CHAPS or CHAPSO.

[17] The reagent according to [15], wherein the bile acid derivative having nonionic surfactant function is BIGCHAP or deoxy-BIGCHAP.

[18] The reagent according to any one of [13] to [17], wherein the polyoxyethylene nonionic surfactant is polyoxyethylene alkylphenyl ether.

[19] A method of suppressing an interference of hemoglobin in immunoassaying a component to be measured in a sample containing hemoglobin, which comprises reacting a component to be measured in a sample containing hemoglobin with an antibody capable of binding to the component in the presence of a bile acid derivative different from a bile acid derivative that is inherently contained in the sample.

[20] The method according to [19], wherein the bile acid derivative different from a bile acid derivative that is inherently contained in the sample is a bile acid derivative having amphoteric surfactant function.

[21] The method according to [19], wherein the bile acid derivative different from a bile acid derivative that is inherently contained in the sample is a bile acid derivative having nonionic surfactant function.

[22] The method according to [20], wherein the bile acid derivative having amphoteric surfactant function is CHAPS or CHAPSO.

[23] The method according to [21], wherein the bile acid derivative having non-ionic surfactant function is BIGCHAP or deoxy-BIGCHAP.

[24] The method according to any one of [19] to [23], which comprises reacting a component to be measured in a sample containing hemoglobin with an antibody capable of binding to the component, further in the presence of a polyoxyethylene nonionic surfactant.

Effects Of The Invention

The present invention provides a method of immunoassaying and a reagent therefor that enable accurate measurement of a component to be measured in a sample containing hemoglobin, and also provides a method of suppressing an interference of hemoglobin in a method of immunoassaying a component to be measured in a sample containing hemoglobin.

BEST MODE FOR CARRYING OUT THE INVENTION (1) Sample Containing Hemoglobin

Examples of the sample containing hemoglobin used in the method of immunoassaying of the present invention include a sample containing hemoglobin and a sample suspected to contain hemoglobin. Examples of the sample containing hemoglobin and the sample suspected to contain hemoglobin include whole blood, blood cell fraction containing red blood cells prepared from whole blood, plasma or serum suspected of hemolysis, red blood cells, and arbitrary samples with added hemoglobin. As to the whole blood, blood itself collected from a subject as well as blood subjected to treatment can be used, and is preferably blood subjected to treatment. Examples of such treatment include anticoagulation treatment and hemolysis treatment, and these treatments may be used in combination.

In case the component to be measured is an intracellular component of a blood cell, the whole blood is preferably blood subjected to hemolysis treatment and is, in particular, preferably blood subjected to both anticoagulation treatment and hemolysis treatment. Examples of the anticoagulation treatment include a treatment in which EDTA, heparin, or such is added to the collected blood. Examples of the hemolysis treatment include addition of a surfactant or saponin solution, mixing with a hypotonic solution, freeze-thawing, and sonication.

(2) Component to be Measured

The component to be measured in the present invention is not particularly limited as long as it is a component in a sample that may contain hemoglobin, and examples of the component include a nucleic acid, a protein, a lipid, a vitamin, and a polysaccharide. Examples of the nucleic acid include DNA, RNA, ATP, ADP, AMP, and cyclic AMP. Examples of the protein include an enzyme, a hormone, and various types of peptides.

The preferred component in the present invention includes a substance contained within the cell, and a protein induced within cells by various cytokines such as interferon.

A specific example of the component is MxA protein induced within cytoplasm by type-I interferon (Mol. Cell. Biol., 9, 5062-5072, 1989; J. Virol. 64, 1171-1181, 1990).

(3) Bile Acid Derivative

The bile acid derivative in the present invention is a bile acid derivative different from a bile acid derivative that is inherently contained in the sample. The bile acid derivative different from a bile acid derivative that is inherently contained in the sample is not particularly limited, as long as it is a bile acid derivative that enables the method of immunoassaying and the method of suppressing an interference of hemoglobin of the present invention, and is preferably a bile acid derivative having amphoteric surfactant function or nonionic surfactant function.

Examples of the bile acid derivative having amphoteric surfactant function include 3-[(3-cholamidopropyl)dimethylammonio]propanesulfonate (hereinafter, abbreviated as CHAPS) and 3-[(3-cholamidopropyl)dimethylammonio]-2-hydroxypropanesulfonate (hereinafter, abbreviated as CHAPSO).

Examples of the bile acid derivative having nonionic surfactant function include N,N-bis(3-D-gluconamidopropyl)cholamide (hereinafter, abbreviated as BIGCHAP) and N,N-bis(3-D-gluconamidopropyl)deoxycholamide (hereinafter, abbreviated as deoxy-BIGCHAP).

The bile acid derivative shows an effect of suppressing an interference of hemoglobin in the reaction of the component to be measured and an antibody capable of binding to the component, and in particular, CHAPS, CHAPSO, BIGCHAP, and deoxy-BIGCHAP are preferably used.

The bile acid derivative is used at a concentration in the range of 1- to 50-times the critical micelle concentration (cmc), and in particular, 1- to 10-times the cmc concentration is preferred. In the present invention, the bile acid derivative can be used alone (one type), or in combination of two or more types of bile acid derivatives.

(4) Polyoxyethylene Nonionic Surfactant

Polyoxyethylene nonionic surfactant works to increase a measurement sensitivity in the method of immunoassaying of the present invention, and are preferably present during the immunoreaction.

Examples of the polyoxyethylene nonionic surfactant in the present invention include polyoxyethylene alkylphenyl ether, polyoxyethylene alkyl ether, and polyoxyethylene sorbitan fatty acid ester, and is preferable polyoxyethylene alkylphenyl ether. Examples of the alkyl in the polyoxyethylene alkylphenyl ether include octyl and nonyl. A specific example (commercially available product) of polyoxyethylene alkylphenyl ether is Nonidet P-40 (polyoxyethylene nonylphenyl ether).

In the present invention, the polyoxyethylene nonionic surfactant can be used alone (one type), or in combination of two or more types of polyoxyethylene nonionic surfactants. In the method of immunoassaying of the present invention, the concentration of the polyoxyethylene nonionic surfactant is preferably 0.01% to 2.0%, more preferably 0.05% to 1.8%, and particularly preferably 0.1% to 1.4%.

(5) Antibody and Labeled Antibody

The antibody used in the method of immunoassaying of the present invention is not particularly limited, as long as it is an antibody that specifically binds to the component to be measured; and either a polyclonal antibody or a monoclonal antibody may be used, but a monoclonal antibody is preferred. Furthermore, the antibody to be used in the present invention includes an antibody fragment. Specific examples include an antibody fragment in which the Fc portion has been removed, such as Fab obtained by papain treatment of an antibody, $F(ab')_2$ obtained by pepsin treatment, and Fab' obtained by pepsin treatment and reduction treatment. In particular, the preferred antibody fragment is $F(ab')_2$.

The antibody to be used in the present invention can be obtained by standard methods using the component to be measured or a part thereof as an antigen, and a commercially available product can be also be used.

In case the component to be measured is MxA protein, examples of the antibody that specifically binds to MxA protein include anti-human MxA protein monoclonal antibodies KM1122, KM1123, KM1124, KM1125, KM1126, KM1127, KM1128, KM1129, KM1130, KM1131, KM1132, KM1133, KM1134, and KM1135 produced by hybridoma cell lines KM1122, KM1123, KM1124 (FERM BP-4729), KM1125, KM1126, KM1127, KM1128, KM1129, KM1130, KM1131, KM1132 (FERM BP-4730), KM1133, KM1134, and KM1135 (FERM BP-4731), respectively, which are described in International Publication No. WO 96/05230.

The labeled antibody in the present invention is an antibody that may be used for the method of immunoassaying a component to be measured in the present invention, and is produced by a method, described later, using the antibody used in the present invention and a labeling substance described below.

(6) Competitive Substance and Labeled Competitive Substance

In the present invention, the term "competitive substance" refers to a substance that can bind to "an antibody capable of binding to a component to be measured" to be used in the method of immunoassaying of the present invention, and competes against the component for binding; and the component itself is also included. A "competitive substance" is used in a measurement of a component to be measured in a sample using a competitive method. Therefore, the antibody capable of binding to a component to be measured used in the competitive method is an antibody capable of binding to a component to be measured, a competitive substance, and a labeled competitive substance. While the antibody binds to the component to form an immune complex, it also binds to the competitive substance to form an immune complex.

The competitive substance is preferably a substance structurally identical to an epitope recognized by the antibody capable of binding to a component to be measured. In addition, as to the ability of binding to the antibody capable of binding to the component to be measured, the competitive substance has, preferably, a comparable level to the component. As the competitive substance, the component to be measured itself is preferred.

The labeled competitive substance in the present invention is a substance that can be used for the method of immunoassaying a component to be measured of the present invention, and is produced by a method described later, using the above-described competitive substance and a labeling substance to be described later.

(7) Method of Immunoassaying

The method of immunoassaying of the present invention is an immunoassay of measuring a component to be measured in a sample containing hemoglobin, which comprises reacting the component in the sample containing hemoglobin with an antibody capable of binding to the component in the presence of a bile acid derivative different from a bile acid derivative that is inherently contained in the sample.

A ratio of the sample containing hemoglobin and a bile acid derivative different from a bile acid derivative that is inherently contained in the sample is preferably 1:1 to 1:1000, and in case the sample containing hemoglobin is whole blood, a ratio of 1:2 to 1:49 is preferred, and a ratio of 1:4 to 1:9 is particularly preferred. When adding the bile acid derivative different from a bile acid derivative that is inherently contained in the sample to the sample containing hemoglobin, the temperature during the addition is preferably approximately 2° C. to 40° C., and measurement is, preferably, carried out within 24 hours after the addition.

The method of immunoassaying is not particularly limited as long as it is a method based on an antigen-antibody reaction, and there are no restrictions on a method of operation, a presence or absence of a labeling substance, a type of labeling substance, a carrier, and a presence or absence of B/F separation.

The antigen-antibody reaction may either be a competitive reaction method or a non-competitive reaction method.

The detection method may either be an unlabeling-method in which the result of antigen-antibody reaction by agglutination or such is detected directly, or a labeling-method in which the result of antigen-antibody reaction is detected using a labeling substance, and the labeling method is particularly preferred from the aspect of measurement sensitivity.

In the method of immunoassaying of the present invention, either a heterogeneous method that requires B/F separation, or a homogeneous method that does not require a B/F separation can be used.

As to a reaction phase, either a liquid phase method in which all reactions are performed in liquid phase, or a solid phase method in which reactions are performed in the state of one part of the reactants in the immune reaction being immobilized to a solid phase, can be used.

Specific examples of the measurement method include the method described in "Bio Kensayaku Kaihatsu Manual (Biological Diagnostic Agent Development Manual)", CMC; jointly-edited by Ishikawa, E. et al. "Koso Meneki Sokuteiho (Enzyme Immunoassay)" 3rd edition, Igaku-Shoin; and Document, Nippon Rinsho (Japanese Journal of Clinical Medicine), Vol. 53, No. 9.

The methods of Measurement Methods 1 to 4 are shown below as specific examples of the method of immunoassaying of the present invention, but the present invention is not limited thereto. Measurement Method 1 is a sandwich method which is a non-competitive reaction method, Measurement Methods 2 and 3 are competitive methods in which a component to be measured in a sample competes with a competitive substance, and Measurement Method 4 is a homogeneous method in which separation of the immune complex from labeled antibody or labeled competitive substance which is not contained in the immune complex (B/F separation) is not carried out.

Measurement Method 1

A measurement method in which steps (a) to (e) below are carried out sequentially:

(a) reacting a component to be measured in a sample containing hemoglobin with a first antibody that binds specifically to the component, in the presence of a bile acid derivative different from a bile acid derivative that is inherently contained in the sample, or in the presence of a bile acid derivative different from a bile acid derivative that is inherently contained in the sample and a polyoxyethylene nonionic surfactant to form an immune complex of the first antibody and the component;

(b) reacting the immune complex produced in step (a) with a labeled second antibody capable of binding to the component, in the presence of a bile acid derivative different from a bile acid derivative that is inherently contained in the sample, or in the presence of a bile acid derivative different from a bile acid derivative that is inherently contained in the sample and a polyoxyethylene nonionic surfactant, to form an immune complex of the first antibody, the component, and the labeled antibody;

(c) separating the immune complex formed in step (b) from the labeled antibody which is not contained in the immune complex;

(d) measuring the amount of label in the immune complex produced in step (b); and (e) determining the concentration of the component in the sample on the basis of the amount of label in the immune complex measured in step (d).

The first antibody is preferably immobilized on an insoluble carrier. Step (a) and step (b) may be performed sequentially or simultaneously. As long as the second antibody can bind to the component bound to the first antibody, the site of the component recognized by the first antibody may be the same as or different from the site of the component recognized by the second antibody, and these sites are preferably different. Furthermore, as described later, in step (e), the concentration of the component in the sample can be determined by using a calibration curve that shows the relationship between the concentrations of the component and the measured values (amount of information originated from label) prepared in advance using the components with known concentrations.

Measurement Method 2

A measurement method in which steps (a) to (d) below are carried out sequentially:

(a) reacting a component to be measured in a sample containing hemoglobin and a labeled competitive substance with an antibody capable of binding to both of the component and the labeled competitive substance, in the presence of a bile acid derivative different from a bile acid derivative that is inherently contained in the sample or in the presence of a bile acid derivative different from a bile acid derivative that is inherently contained in the sample and a polyoxyethylene nonionic surfactant, to form an immune complex of the antibody and the labeled competitive substance, and an immune complex of the antibody and the component;

(b) separating the immune complex of the antibody and the labeled competitive substance from unreacted labeled competitive substance;

(c) measuring the amount of label in the immune complex of the antibody and the labeled competitive substance formed in step (a); and (d) determining the concentration of the component in the sample on the basis of the amount of label in the immune complex measured in step (c).

The antibody is preferably immobilized on an insoluble carrier. Furthermore, as described later, in step (d), the concentration of the component in the sample can be determined by using a calibration curve that shows the relationship between the concentration of the component and the measured values (amount of information originated from label) prepared in advance using the component with known concentrations.

Measurement Method 3

A measurement method in which steps (a) to (d) below are carried out sequentially:

(a) reacting a component to be measured in a sample containing hemoglobin and a competitive substance with a labeled antibody produced by binding a label to an antibody capable of binding to both of the component and competitive substance, in the presence of a bile acid derivative different from a bile acid derivative that is inherently contained in the sample, or in the presence of a bile acid derivative different from a bile acid derivative that is inherently contained in the sample and a polyoxyethylene nonionic surfactant, to form an immune complex of the labeled antibody and the competitive substance, and an immune complex of the labeled antibody and the component;

(b) separating the immune complex of the labeled antibody and the competitive substance from unreacted labeled antibody and the immune complex of the labeled antibody and the component;

(c) measuring the amount of label in the immune complex of the labeled antibody and competitive substance; and (d) determining the concentration of the component in the sample on the basis of the amount of label in the immune complex measured in step (c).

The competitive substance is preferably immobilized on an insoluble carrier. In case the competitive substance has the same structure as the component, a competitive substance immobilized on an insoluble carrier is used in step (a). Furthermore, as described later, in step (d), the concentration of the component in the sample can be determined by using a calibration curve that shows the relationship between the concentrations of the component and the measured values (amount of information originated from label) prepared in advance using the components with known concentrations.

Measurement Method 4

A measurement method comprising steps (a) to (c) below:
(a) reacting a component to be measured in a sample containing hemoglobin with labeled antibody 1 in which a first antibody capable of binding to the component is labeled with labeling substance 1, and with labeled antibody 2 in which a second antibody capable of binding to the component is labeled with labeling substance 2, different from labeling substance 1, in the presence of a bile acid derivative different from a bile acid derivative that is inherently contained in the sample, or in the presence of a bile acid derivative different from a bile acid derivative that is inherently contained in the sample and a polyoxyethylene nonionic surfactant, to form an immune complex of labeled antibody 1, the component, and labeled antibody 2;
(b) measuring the amount of change in the interaction between labeling substance 1 and labeling substance 2 in the immune complex formed in step (a); and
(c) determining the amount of the component in the sample on the basis of the amount of change of interaction measured in step (b).

As long as the second antibody can bind to the component bound to the first antibody, the site of the component recognized by the first antibody may be the same as or different from the site of the component recognized by the second antibody, and these sites are preferably different. Furthermore, as described later, in step (c), the concentration of the component in the sample can be determined by using a calibration curve that shows the relationship between the concentrations of the component and the measured values (amount of information originated from label) prepared in advance using the components with known concentrations.

As described above, Measurement Methods 1 to 3 are heterogeneous methods that involve B/F separation. Step (c) of Measurement Method 1 and step (b) of Measurement Methods 2 and 3 are steps of B/F separation. In case an antibody or a competitive substance is immobilized on an insoluble carrier, B/F separation can be performed easily by removing the reaction solution and then washing the insoluble carrier. More specifically, by removing the reaction solution after the antigen-antibody reaction, and washing the insoluble carrier with a washing solution, the immune complexes formed on the insoluble carrier can be separated from unreacted labeled substances (labeled antibody and labeled competitive substance).

Examples of the washing solution include phosphate buffered saline (pH 7.2, 10 mmol/L phosphate buffer containing 0.15 mol/L sodium chloride; hereinafter referred to as PBS), PBS containing a surfactant, and an aqueous medium described later. Examples of the surfactant include a nonionic surfactant such as Tween 20.

Furthermore, in Measurement Method 1, when the first antibody is immobilized on an insoluble carrier, a step of washing the insoluble carrier can be inserted between step (a) and step (b) to remove unreacted reactants. In this case, step (b) becomes the step of reacting the immune complex formed in step (a) with a labeled second antibody capable of binding to the component, to form an immune complex of the first antibody, the component, and the labeled antibody.

In Measurement Method 2, in case the antibody capable of binding to the component is not immobilized on an insoluble carrier, in step (c), an insoluble carrier immobilized with a binding substance incapable of binding to the labeled competitive substance and capable of binding to the antibody is allowed to react with the immune complexes to give the immune complex bound to the insoluble carrier. After the reaction solution is removed, the insoluble carrier is washed to separate the immune complexes from the labeled competitive substance which is not contained in the immune complex. Furthermore, in the presence of an insoluble carrier immobilized with a binding substance incapable of binding to the labeled competitive substance and capable of binding to the antibody, a reaction of formation of the immune complexes of step (a) is carried out to give a formation of the immune complexes and an immobilization of the immune complexes to the insoluble carrier simultaneously, and removal of the reaction solution followed by washing of the insoluble carrier lead to separation of the immune complexes from labeled competitive substance which is not contained in the immune complex. Examples of the binding substance incapable of binding to the labeled competitive substance and capable of binding to the antibody include an antibody capable of binding to the constant region of the antibody. In case the component is not a protein, a protein precipitant such as ammonium sulfate or polyethylene glycol can be added in step (c) to precipitate only the immune complex. After centrifugation of the reaction mixture, the immune complex can be separated from labeled competitive substance which is not contained in the immune complex.

In Measurement Method 1, in case the first antibody is not immobilized on an insoluble carrier, separation of the labeled antibody contained in the immune complex from the labeled antibody which is not contained in the immune complex can be carried out by addition of an insoluble carrier immobilized with a binding substance incapable of binding to the labeled antibody and capable of binding to the first antibody in the step of B/F separation, followed by removal of a reaction solution and washing of the insoluble carrier. Furthermore, separation of the labeled antibody contained in the immune complex from the labeled antibody which is not contained in the immune complex can be carried out by formation of the immune complexes in the presence of an insoluble carrier immobilized with a binding substance incapable of binding to the labeled antibody and capable of binding to the first antibody in the step of formation of the immune complexes, followed by removal of a reaction solution and washing of the insoluble carrier. Examples of the binding substance incapable of binding to the labeled antibody and capable of binding to the first antibody include an antibody against immunoglobulin of animal species used to produce the first antibody, in case the animal species used to produce the first antibody is different from the animal species used to produce the antibody (second antibody) used for the labeled antibody; and an antibody capable of specifically binding to the constant region of the first antibody, in case the first antibody is an antibody with constant region and the labeled antibody is an antibody fragment such as Fab or $F(ab')_2$, or Fab' that does not have constant region.

(8) Insoluble Carrier

The insoluble carrier for immobilizing an antibody or a competitive substance is not restricted as long as it can stably hold the antibody or the competitive substance. Examples of the preferred material for the insoluble carrier include a polymer material such as polystyrene, polycarbonate, polyvinyl toluene, polypropylene, polyethylene, polyvinyl chloride, nylon, polymethacrylate, gelatin, agarose, cellulose, nitrocellulose, cellulose acetate, cellulose acetate, and polyethylene terephthalate, glass, ceramics, magnetic particle, and metal. Examples of the preferred form of insoluble carrier include tube, bead, plate, microparticle such as latex, and stick. For example, a polystyrene microtiter plate having 96 wells per plate is preferred.

(9) Immobilization of an Antibody or a Competitive Substance to an Insoluble Carrier Examples of the method of immobilizing an antibody or a competitive substance to an insoluble carrier include a known method such as a method using a physical bond, a method using a chemical bond, or a combination thereof. Examples of the physical bond include an electrostatic bond, a hydrogen bond, and a hydrophobic bond. Examples of the chemical bond include a covalent bond and a coordinate bond. In case using a polystyrene microtiter plate for the method of immunoassay as an insoluble carrier, a method of immobilization is exemplified that addition of a solution of an antibody or a competitive substance to the wells of the plate is followed by incubation for one hour to one day at 4° C. to 30° C. for physical adsorption.

The antibody or the competitive substance can be immobilized directly or indirectly on an insoluble carrier. Examples of the indirect immobilization include a method comprising adding a biotinylated antibody or a biotinylated competitive substance to an insoluble carrier immobilized with avidin, and immobilizing the antibody or the competitive substance to the insoluble carrier through specifically binding between biotin and avidin. Furthermore, an antibody capable of specifically binding to the antibody or an antibody capable of specifically binding to the competitive substance can be immobilized on the insoluble carrier, and the antibody or the competitive substance can be immobilized on the insoluble carrier through such an antibody. Alternatively, the antibody or the competitive substance may be immobilized on the insoluble carrier by covalent bonds via a linker.

The linker is not restricted as long as it can form a covalent bond between both a functional group of the antibody or the component and a functional group of the side chain of the insoluble carrier. In a preferred embodiment, for example, it is a molecule that concurrently has a first reactive group that can react with a functional group of the antibody or the component, and a second reactive group that can react with a functional group of the side chain of the insoluble carrier. Preferably, the first reactive group is different from the second reactive group. Examples of the functional group of the antibody or the competitive substance, and the functional group that the insoluble carrier has on its surface, include carboxy group, amino group, glycidyl group, sulfhydryl group, hydroxy group, amide group, imino group, N-hydroxysuccinyl group, and maleimide group. Examples of the reactive group on the linker include groups such as arylazide, carbodiimide, hydrazide, aldehyde, hydroxymethyl phosphine, imide ester, isocyanate, maleimide, N-hydroxy succinimide (NHS) ester, pentafluorophenyl (PFP) ester, psoralen, pyridyl disulfide, and vinyl sulfone.

(10) Labeling of an Antibody or a Component to be Measured

Examples of the labeling substance for labeling an antibody or a component to be measured include an enzyme, a fluorescent substance, a luminescent substance, a radioisotope, biotin, digoxigenin, a polypeptide containing a tag sequence, a metallic colloid particle, and a colored latex particle.

Examples of the enzyme include alkaline phosphatase, peroxidase, galactosidase, glucuronidase, and luciferase.

Examples of the fluorescent substance include fluorescein isothiocyanate (FITC) and rhodamine B-isothiocyanate (RITC). Examples of the other fluorescent substance include quantum dot (Science, 281, 2016-2018, 1998), phycobiliprotein such as phycoerythrin, and a fluorescence-emitting protein such as green fluorescent protein (GFP), red fluorescent protein (RFP), yellow fluorescent protein (YFP), and blue fluorescent protein (BFP).

Examples of the luminescent substance include acridinium and a derivative thereof, a ruthenium complex compound, and lophine. As to the ruthenium complex compound, the compound that electrochemically emits light with electron donors (described in Clin. Chem. 37, 9, 1534-1539, 1991) is preferred.

Examples of the radioisotope include $^{3}H$, $^{14}C$, $^{35}S$, $^{32}P$, $^{125}I$, and $^{131}I$.

Examples of the polypeptide containing a tag sequence include the FLAG peptide (FLAG tag, Asp Tyr Lys Asp Asp Asp Asp Lys), polyhistidine (His tag, His His His His His His), myc epitope peptide (myc tag, Glu Gln Lys Leu Ile Ser Glu Glu Asp Leu), and hemagglutinin epitope peptide (HA tag, Tyr Pro Tyr Asp Val Pro Asp Tyr Ala).

Labeling of the antibody or the component to be measured can be carried out by a reaction that forms a covalent bond between the functional group of the antibody or the component and the functional group of the labeling substance, either with or without a linker. Examples of the functional group include a carboxyl group, an amino group, a glycidyl group, a sulfhydryl group, a hydroxy group, an amido group, an imino group, a hydroxysuccinyl ester group, a maleimide group, and an isothiocyanate group. A condensation reaction between these functional groups can be performed.

Examples of the method of formation of bond without a linker include a method using a carbodiimide compound such as EDC. In this case, an active ester such as NHS or its derivatives can be used. The condensation reaction between an isothiocyanate group and an amino group is preferred because it does not require other reagents, and proceeds simply by mixing under neutral to weakly alkaline conditions.

The linker is not restricted, as long as it can make a bond between the labeling substance and the antibody via their respective functional groups. In a preferred embodiment, for example, the linker is a molecule that has within the same molecule a first functional group that can react with an amino acid residue of the antibody, and a second functional group that can react with a functional group of the side chain of the labeling substance. Preferably, the first functional group is different from the second functional group. Examples of the functional group of the linker include the functional groups described above.

Examples of the method of making a radioisotope bond chemically include the method described in Antibody Immunoconj. Radiopharm., 3, 60, 1990.

In case the labeling substance is an enzyme, avidin, a fluorescence-emitting protein, a phycobiliprotein, or a polypeptide such as a polypeptide comprising a tag sequence, the labeled antibody can be produced as follows: producing an expression vector containing a DNA that encodes a fusion protein of the labeling substance and the antibody, introducing the expression vector into a suitable host, and culturing the host (Molecular Cloning: A Laboratory Manual, 3rd Edition, Cold Spring Harbor Laboratory Press, 2001). A DNA encoding the fusion protein can be obtained by cloning using PCR or the like of DNAs that encode individually the antibody and the labeling substance, and linking each of the DNAs by a ligase reaction.

Examples of the labeling substances 1 and 2 used in the homogeneous method described in Measurement Method 4 of the above-mentioned (6) include labeling substances that initiate an interaction by binding to a component to be measured and coming near thereby. Examples of such labeling substances include fluorescent substances that exhibit fluorescence resonance energy transfer (FRET). FRET is a phenomenon that a fluorescent energy produced when the first fluorescent substance is subjected to excitation light is used as a fluorescent energy of the second fluorescent substance near the first fluorescent substance, and takes place when the two kinds of fluorescent substances come near each other to a distance of 1 to 10 nm. Examples of the combination of the fluorescent substances that exhibit FRET include a combination in which the fluorescent wavelength spectrum of one of the substances has some overlap with the excitation wavelength spectrum of the other substance. Examples of the fluorescent substance include a fluorescent protein, a low-molecular-weight organic fluorescent dye, and an inorganic compound. Examples of the combination of fluorescent proteins that exhibit FRET include the combination of YFP [yellow mutant of green fluorescent protein (GFP)] and CFP [cyan mutant of green fluorescent protein (GFP)]. Examples of the combination of low-molecular-weight organic fluorescent dye include a combination of Cy3 and Cy5. Examples of the inorganic compound include quantum dot (Science, 281, 2016-2018, 1998).

Furthermore, examples of the combination of the labeling substances in the homogeneous method include a combination of a chemiluminescence-producing enzyme and a fluorescent substance that exhibit bioluminescence resonance energy transfer (BRET). Examples of the combination of an enzyme and a fluorescent substance that exhibit BRET include a combination that affords an overlap between the luminescence wavelength spectrum formed when the enzyme degrades its substrate and the excitation wavelength spectrum of the fluorescent substance. Examples of the combination include a combination of *Renilla luciferase* (Rluc) as the enzyme, Deep Blue C (manufactured by Packard BioScience) or such as the substrate, and GFP as the fluorescent substance. In this case, a light having a wavelength of 395 nm is produced by degradation of the substrate by Rluc; and as GFP comes near Rluc, GFP receives the energy of this light and emits fluorescence at wavelength 510 nm which can be detected.

Examples of the combination of the labeling substances in the homogeneous method include a combination of substances in which enzyme activity appears when labeling substance 1 and labeling substance 2 come near each other and bind in a certain orientation. Examples of the combination of the labeling substances include a combination of the Δα subunit of β-galactosidase as labeling substance 1 and the Δω subunit of β-galactosidase as labeling substance 2, and a combination of the N-terminal domain of Rluc as labeling substance 1 and the C-terminal domain of Rluc as labeling substance 2.

(11) Antigen-antibody Reaction

An antigen-antibody reaction is preferably performed in an aqueous medium. The reaction temperature is, for example, 0° C. to 50° C., and is preferably 4° C. to 40° C. The reaction time is preferably 5 minutes to 20 hours.

(12) Measurement of the Amount of Label

A suitable method of measuring the amount of label in the immune complex can be selected according to the labeling substance. More specifically, in case the labeling substance is a coloring substance which is a substance that absorbs light of a certain wavelength or the amount of change in turbidity (absorbance) caused by agglutination or the like is measured, a spectrophotometer, a multi-well plate reader, or such can be used. In case the labeling substance is a fluorescent substance, a spectrofluorometer, fluorescence multi-well plate reader, or such may be used. When the labeling substance is a luminescent substance, a luminescence photometer, luminescence multi-well plate reader, or such can be used. In case the labeling substance is a radioisotope, the amount of radioisotope can be determined by measuring the radioactivity using a scintillation counter, a γ-well counter, or such.

In case the label is an enzyme, the amount of the label can be determined by measuring enzyme activity. For example, the amount of the label can be determined by reacting a substrate of the enzyme with the enzyme and measuring the substance formed.

In case the enzyme is peroxidase, peroxidase activity can be measured, for example, by a spectrophotometry, a fluorescence spectrophotometry, or such. Examples of the method of measuring peroxidase activity by a spectrophotometry include a method comprising reacting of peroxidase with a combination of hydrogen peroxide and an oxidative coloring chromogen, which are the substrates of peroxidase, and measuring the absorbance of the reaction solution using a spectrophotometer or multi-well plate reader. Examples of the oxidative coloring chromogen include a leuco-type chromogen and an oxidative coupling-coloring chromogen.

The leuco-type chromogen is a substance that is converted into a dye by itself in the presence of hydrogen peroxide and a peroxidative substance such as peroxidase. Specific examples include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino) diphenylamine sodium salt (DA-64), 4,4'-bis(dimethylamino)diphenylamine, and bis[3-bis(4-chlorophenyl)methyl-4-dimethylaminophenyl]amine (BCMA).

The oxidative coupling-coloring chromogen is a substance that forms a dye by oxidative coupling of two compounds in the presence of hydrogen peroxide and a peroxidative substance such as peroxidase. Examples of the combination of two compounds include a combination of a coupler and an aniline compound (Trinder reagent), and a combination of a coupler and a phenol compound. Examples of the coupler include 4-aminoantipyrine (4-AA) and 3-methyl-2-benzothiazolinonehydrazine. Examples of the aniline compound include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl) aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS). Examples of the phenol compound include phenol, 4-chlorophenol, 3-methylphenol, and 3-hydroxy-2,4,6-triiodobenzoic acid (HTIB).

Examples of the method of measuring the peroxidase activity by a fluorescence spectrometry include a method comprising reacting of peroxidase with a combination of hydrogen peroxide and a fluorescent substance, which are the substrates of peroxidase, and measuring the intensity of the generated fluorescence using a spectrofluorometer, fluorescence multi-well plate reader, or the like. Examples of the fluorescent substance include 4-hydroxyphenylacetic acid, 3-(4-hydroxyphenyl)propionic acid, and coumarin.

Examples of the method of measuring the peroxidase activity by a luminescent measurement include a method comprising reacting of peroxidase with a combination of hydrogen peroxide and a luminescent substance, which are the substrates of peroxidase, and measuring the intensity of the generated luminescence using a luminescence intensity meter, luminescence multi-well plate reader, or the like. Examples of the luminescent substance include a luminol compound and a lucigenin compound.

In case the enzyme is alkaline phosphatase, the alkaline phosphatase activity can be measured by, for example, a luminescent measurement. Examples of the method of measuring the alkaline phosphatase activity by a luminescent measurement include a method comprising reacting of alkaline phosphatase with its substrate, and measuring the luminescence intensity of the generated luminescence using a luminescence intensity meter, luminescence multi-well plate reader, or the like. Examples of the substrate of alkaline phosphatase include 3-(2'-spiroadamantane)-4-methoxy-4-(3'-phosphoryloxy)phenyl-1,2-dioxetane disodium salt (AMPPD), 2-chloro-5-{4-methoxyspiro[1,2-dioxetane-3,2'-(5'-chloro)tricyclo[3.3.1.13,7]decane]-4-yl}phenylphosphate disodium salt (CDP-Star™), 3-{4-methoxyspiro[1,2-dioxetane-3,2'-(5'-chloro)tricyclo[3.3.1.13,7]decane]-4-yl}phenylphosphate disodium salt (CSPD™), and [10-methyl-9(10H)-acridinylidene]phenoxymethylphosphate disodium salt (Lumigen™ APS-5).

In case the enzyme is β-D-galactosidase, the β-D-galactosidase activity can be measured by, for example, a spectrophotometry (colorimetric method), a luminescent measurement, or a fluorescence spectrophotometry. Examples of the method of measuring the β-D-galactosidase activity by a spectrophotometry (colorimetric method) include a method using o-nitrophenyl-β-D-galactopyranoside. Examples of the method of measuring the β-D-galactosidase activity by a luminescent measurement include a method comprising reacting of β-D-galactosidase with its substrate, and measuring the luminescence of the reaction solution by a luminescence intensity meter, luminescence multi-well plate reader, or the like. Examples of the substrate of β-D-galactosidase include Galacton-Plus (manufactured by Applied Biosystems), and analogs thereof. Examples of the method of measuring the β-D-galactosidase activity by a fluorescence spectrophotometry include a method comprising reacting of β-D-galactosidase with its substrate, and measuring the fluorescence of the reaction solution by a spectrofluorometer, fluorescence multi-well plate reader, or the like. Examples of the substrate of β-D-galactosidase include 4-methylumbeliferyl-β-D-galactopyranoside.

In case the enzyme is luciferase, the luciferase activity can be measured, for example, by a luminescent measurement. Examples of the method of measuring the luciferase activity by a luminescent measurement include a method comprising reacting of luciferase with its substrate, and measuring the luminescence of the reaction solution by a luminescence intensity meter, luminescence multi-well plate reader, or the like. Examples of the substrate of luciferase include luciferin and coelenterazine.

In case the labeling substance is those other than a fluorescent substance, a luminescent substance, a radioisotope, or an enzyme, detection can be carried out according to a method Comprising: allowing a labeled substance, in which a substance capable of specifically binding to the labeling substance is labeled with a fluorescent substance, a luminescent substance, a radioisotope, an enzyme or the like, to bind with the labeling substance constituting the labeled antibody or the labeled competitive substance of the immune complex; making the measurement by using the fluorescent substance, the luminescent substance, the radioisotope, or the enzyme, which label the substance capable of binding to the labeling substance, as described above. Examples of the substance capable of specifically binding to the labeling substance include an antibody capable of specifically binding to the labeling substance, avidin or streptavidin which are the substances capable of specifically binding to biotin (the labeling substance). Furthermore, detection can be carried out according to a method comprising: allowing a substance capable of specifically binding to the labeling substance, such as an antibody capable of specifically binding to the labeling substance, and avidin or streptavidin, to bind with labeling substance of the immune complex; then allowing a labeled antibody to bind with the labeling substance, wherein the labeled antibody is formed by labeling an antibody capable of binding to the substance which is capable of specifically binding to the labeling substance (examples of the antibody include an antibody capable of specifically binding to a constant region of an antibody, and an antibody capable of specifically binding to avidin or streptavidin) with a fluorescent substance, a luminescent substance, a radioisotope, an enzyme or the like; and making the measurement by using the fluorescent substance, the luminescent substance, the radioisotope, or the enzyme, as described above.

The antibody used in such detection, the antibody capable of specifically binding to avidin or streptavidin or the labeling substance, the antibody capable of specifically binding to a constant region of an antibody, the antibody capable of specifically binding to avidin or streptavidin may be polyclonal or monoclonal antibody, or antibody fragments in which Fc portion has been removed, such as Fab, F(ab')$_2$ obtained by pepsin treatment, and Fab' obtained by pepsin treatment and reduction treatment.

(13) Determination of the Component to be Measured

For determination of the component to be measured, it is necessary to make a calibration curve that shows the relationship between the concentrations of the component and the measured values (amount of information originated from label) using a standard substance, i.e., solutions of the component with known concentrations. The concentration of the component can be determined as follows: making the calibration curve; carrying out the measurement using the sample; and correlating the measured values obtained with the calibration curve produced in advance.

(14) Aqueous Medium and Other Coexisting Substances

Examples of the aqueous medium used in the method of immunoassaying of the present invention include a deionized water, a distilled water, and a buffer, and a buffer is preferred. A buffer agent used for preparing buffer is not particularly limited as long as it has buffering ability. Examples of the buffer include a buffer with pH 1 to 11, such as lactate buffer, citrate buffer, acetate buffer, succinate buffer, phthalate buffer, phosphate buffer, triethanolamine buffer, diethanolamine buffer, lysine buffer, barbiturate buffer, imidazole buffer, malate buffer, oxalate buffer, glycine buffer, borate buffer, carbonate buffer, glycine buffer, or Good's buffer.

Examples of the Good's buffer include 2-morpholinoethanesulfonic acid (MES) buffer, bis(2-hydroxyethyl)iminotris(hydroxymethyl)methane (Bis-Tris) buffer, tris(hydroxymethyl)aminomethane (Tris) buffer, N-(2-acetoamido) imino diacetic acid (ADA) buffer, piperazine-N,N'-bis(2-ethanesulfonic acid) (PIPES) buffer, 2-[N-(2-acetamido) amino]ethanesulfonic acid (ACES) buffer, 3-morpholino-2-hydroxypropanesulfonic acid (MOPSO) buffer, 2-[N,N-bis (2-hydroxyethyl)amino]ethanesulfonic acid (BES) buffer, 3-morpholinopropanesulfonic acid (MOPS) buffer, 2-{N-[tris(hydroxymethyl)methyl]amino}ethanesulfonic acid (TES) buffer, N-(2-hydroxyethyl)-N'-(2-sulfoethyl)piperazine (HEPES) buffer, 3-[N,N-bis(2-hydroxyethyl)amino]-2-hydroxypropanesulfonic acid (DIPSO) buffer, 2-hydroxy-3-{[N-tris(hydroxymethyl)methyl]amino}propanesulfonic acid (TAPSO) buffer, piperazine-N,N'-bis(2-hydroxypropane-3-sulfonic acid) (POPSO) buffer, N-(2-hydroxyethyl)-N'-(2-hydroxy-3-sulfopropyl)piperazine (HEPPSO) buffer, N-(2-hydroxyethyl)-N'-(3-sulfopropyl)piperazine (EPPS) buffer, tricine[N-tris(hydroxymethyl)methylglycine] buffer, vicine[N,N-bis(2-hydroxyethyl)glycine] buffer, 3-[N-tris (hydroxymethyl)methyl]aminopropanesulfonic acid (TAPS) buffer, 2-(N-cyclohexylamino)ethanesulfonic acid (CHES) buffer, 3-(N-cyclohexylamino)-2-hydroxypropanesulfonic acid (CAPSO) buffer, and 3-(N-cyclohexylamino)propanesulfonic acid (CAPS) buffer.

The concentration of the buffer is not particularly limited as long as it is a concentration suitable for the measurement, and is preferably 0.001 to 2.0 mol/L, more preferably 0.005 to 1.0 mol/L, and particularly preferably 0.01 to 0.1 mol/L.

In the method of immunoassaying of the present invention, a metal ion, a salt, a sugar, a surfactant, an antiseptic agent, a protein, a protein stabilizer, or such can be present together.

Examples of the metal ion include magnesium ion, manganese ion, and zinc ion.

Examples of the salt include sodium chloride and potassium chloride.

Examples of the sugar include mannitol and sorbitol.

Examples of the antiseptic agent include sodium azide, an antibiotic (streptomycin, penicillin, gentamicin, etc.), Bio-Ace, Proclin 300, and Proxel GXL.

Examples of the protein include bovine serum albumin (BSA), fetal bovine serum (FBS), casein, and BlockAce (manufactured by Dainippon Pharmaceutical Co., Ltd.).

Examples of the protein stabilizing agent include Peroxidase Stabilizing Buffer (manufactured by DakoCytomation).

(15) Reagent of Immunoassay

The reagent of immunoassay of the present invention can be used for the method of immunoassaying of the present invention, and comprises the bile acid derivative of (3) mentioned above, and if necessary, a polyoxyethylene nonionic surfactant. Examples of the reagent of immunoassay of the present invention include a reagent comprising a component selected from the group consisting of (i) to (iii) below, the bile acid derivative of (3), and if necessary, a polyoxyethylene nonionic surfactant:

(i) a first antibody capable of binding to the component and a labeled second antibody capable of binding to the component;
(ii) a labeled competitive substance and an antibody capable of binding to both of the component and the competitive substance; and
(iii) a competitive substance and a labeled antibody capable of binding to both of the component and the competitive substance.

The form of the reagent of immunoassay of the present invention is not particularly limited, as long as it is a form that enables the method of immunoassaying of the present invention. Examples of forms of the reagent include a liquid form, a freeze-dried form, or the like. In case using a freeze-dried form of reagent, it is used for the measurement after being dissolved in the aforementioned aqueous medium or such.

As to the bile acid derivative, the antibody capable of binding to the component, the competitive substance, the labeled antibody capable of binding to the component, and the labeled competitive substance used in the reagent of immunoassay of the present invention, the aforementioned bile acid derivative, the aforementioned antibody capable of binding to the component, the aforementioned competitive substance, the aforementioned labeled antibody capable of binding to the component, and the aforementioned labeled competitive substance can be used, respectively. Furthermore, the reagent of immunoassay of the present invention can comprise, as necessary, the aforementioned aqueous medium, the aforementioned metal ion, the aforementioned salt, the aforementioned sugar, the aforementioned surfactant, the aforementioned antiseptic agent, the aforementioned protein, the aforementioned protein stabilizer, or such.

Furthermore, the reagent of immunoassay of the present invention can be stored and distributed in the form of a kit. Examples of the kit include a kit composed of two reagents and a kit composed of three reagents, and the components in each of the reagents constituting the kit can be suitably selected by those skilled in the art. For example, a solution prepared by dissolving a bile acid derivative in an aqueous medium can be comprised of the kit as a solution for dilution of a sample, which can be one of the reagents constituting the kit.

(16) Method of Suppressing an Interference of Hemoglobin in a Sample

The present invention provides a method of suppressing an interference of hemoglobin in the method of immunoassaying a component to be measured in a sample containing hemoglobin. The interference of hemoglobin can be suppressed by co-existence of a bile acid derivative different from a bile acid derivative that is inherently contained in the sample, in the method of immunoassaying of the component to be measured. Co-existence of a bile acid derivative different from a bile acid derivative that is inherently contained in the sample, suppresses an interference of hemoglobin in the sample to give an accurate measurement.

Herein below, the present invention will be specifically described with reference to the Examples, which is not to be construed as limiting the scope of the present invention.

EXAMPLE 1

[1] Preparation of Anti-MxA protein monoclonal antibodies

A hybridoma cell line KM1124 (FERM BP-4729) which produces the monoclonal antibody KM1124 and a hybridoma cell line KM1135 (FERM BP-4731) which produces the monoclonal antibody KM1135 were individually intraperitoneally injected into pristane-treated 8-week old nude female mice (Balb/c) at 5 to $20 \times 10^6$ cells/animal. The hybridoma cell cancerated in ascites of mice after 10 to 21 days, and the ascitic fluids were collected from the mice. The collected ascitic fluids were centrifuged at 3000 rpm for five minutes to remove the solid content, and the supernatants were collected. Monoclonal antibodies were purified by the caprylic acid precipitation method (Antibodies—A Laboratory Manual, Cold Spring Harbor Laboratory, 1988) from the supernatants, and the monoclonal antibodies KM1124 and KM1135 were obtained, respectively.

KM1124 is a mouse monoclonal antibody capable of binding to the epitope in residues 220 to 297 counting from the amino terminus of human MxA protein, and KM1135 is a mouse monoclonal antibody capable of binding to the epitope in residues 10 to 220 counting from the amino terminus of human MxA protein.

[2] Preparation of Recombinant MxA Protein

With a human MxA protein expression vector pET14b-MxA (Nucleic Acids Res., 32, 643-652, 2004) produced by inserting an NdeI-BamHI fragment containing a cDNA encoding human MxA protein between NdeI and BamHI of the pET-14b vector (manufactured by Novagen, EMD Biosciences), was transformed the Escherichia coli BL21 (DE3) pLysS strain. This transformant expresses an MxA protein to which an N-terminal His tag has been added.

The obtained transformant was inoculated into 5 mL of LB medium containing ampicillin, and the cells were cultured with shaking at 37° C. until the optical density at 600 nm (OD600) reached 0.5. This culture solution was inoculated into 250 mL of LB medium containing ampicillin, and the cells were cultured with shaking at 37° C. until the optical density at 600 nm reached 0.3 to 0.5. To this culture, isopropylthiogalactoside (IPTG) was added at a final concentration of 0.4 mmol/L, and culturing was completed after two more hours of subsequent culture with shaking at 37° C. The culture solution was centrifuged at 4° C. at 3000 rpm for ten minutes to collect the bacterial cells. The bacterial cells were stored at −80° C. until MxA protein preparation.

Since MxA protein was present in the bacterial cells in the form of inclusion bodies, the bacterial cells were thawed on ice, and 20 mL of ice-cooled binding buffer (5 mmol/L imidazole, 0.5 mol/L sodium chloride, 20 mmol/L Tris-HCl, pH 7.9) was added to give the suspension. The bacterial cell suspension was subjected to five times of 30-second ultrasonic treatment to disrupt the cells, and then centrifuged at 4° C. at 4000 rpm for ten minutes. The supernatant was removed, and the precipitate was suspended in 20 mL of added ice-cooled binding buffer. Similarly, ultrasonic treatment and centrifugation were again performed. The supernatant was removed, and 20 mL of the binding buffer containing 6 mol/L urea was added to the precipitate to give the suspension. After a similar ultrasonic treatment, the mixture was left to stand on ice for 30 minutes to dissolve the inclusion bodies, and then centrifuged at 4° C. at 10,000 rpm for 30 minutes. The supernatant was collected and then filtered through a 0.45-nm millipore filter.

To the obtained solution, 0.5 mL of Ni-NTA His•Bind Resin (manufactured by Novagen, EMD Biosciences) was added, then the whole was mixed while rotating at 4° C. for two hours, and the MxA protein was allowed to bind with the resin via the His tag. This mixture was centrifuged at 4° C. at 3000 rpm for two minutes to recover the resin. After adding 10 mL of ice-cooled binding buffer containing 6 mol/L urea to the resin, the whole was centrifuged at 4° C. at 3000 rpm for two minutes to recover the resin. After repeating this washing operation, 10 mL of ice-cooled washing buffer (6 mol/L urea, 60 mmol/L imidazole, 0.5 mol/L sodium chloride, 20 mmol/L Tris-HCl, pH 7.9) was further added to the resin, and the whole was centrifuged at 4° C. at 3000 rpm for two minutes to recover the resin.

Ten mL of ice-cooled elution buffer (6 mol/L urea, 1 mol/L imidazole, 0.5 mol/L sodium chloride, 20 mmol/L Tris-HCl, pH 7.9) was added to the resin, and the whole was mixed while rotating at 4° C. for two hours to elute the MxA protein from the resin. The mixture was subsequently centrifuged at 4° C. at 3000 rpm for two minutes, and the supernatant was collected as the MxA protein solution.

[3] Preparation of Anti-MxA Protein Antibody-immobilized Plate

The anti-MxA protein monoclonal antibody KM1135 prepared in [1] was diluted with PBS to a concentration of 5 µg/mL, and the mixture was dispensed in a 96-well microtiter plate (manufactured by Nalge Nunc International) at 100 µL/well. After allowing the plate to stand for three days, the supernatant was removed by suction, 25% BlockAce (manufactured by Dainippon Pharmaceutical Co., Ltd.) and 300 µL PBS were dispensed, and blocking was carried out at room temperature by allowing the plate to stand overnight. After removing the blocking solution, washing was carried out using PBS. The plate after drying for three days using a vacuum dryer was used as the anti-MxA protein monoclonal antibody-immobilized plate.

[4] Preparation of Peroxidase-labeled Anti-MxA Protein Antibody

The anti-MxA protein monoclonal antibody KM1124 prepared in [1] was allowed to bind with peroxidase (hereinafter, abbreviated as POD) by the maleimide method as described below to give a POD-labeled anti-MxA protein antibody.

First, the solvent of a solution containing 2 mg of the anti-MxA protein antibody KM1124 was substituted with 0.1 mol/L borate buffer (pH 8.0), and 0.086 mg of 2-iminothiolane hydrochloride (manufactured by PIERCE) was added. The mixture was stirred and the reaction was continued at 30° C. for 30 minutes after stirring. Using a Sephadex G25 (manufactured by Amersham Bioscience) column (1.5 cm diameter×30 cm) equilibrated with 0.1 mol/L phosphate buffer (pH 6.0), unreacted 2-iminothiolane in the reaction solution was removed and sulfhydrylated KM1124 was collected.

Meanwhile, 2.5 mg of POD (manufactured by TOYOBO, peroxidase I-C), which corresponds to 5-times the amount of the anti-MxA protein antibody KM 1124 in terms of molar ratio, was dissolved in 250 µL, of 0.1 mol/L phosphate buffer (pH 7.0). After warming this solution at 30° C. for five minutes, 0.72 mg of N-(6-maleimidocaproyloxy)succinimide (EMCS, manufactured by DOJINDO Laboratories) dissolved in N,N-dimethylformamide (manufactured by Nacalai Tesque) was added, and the mixture was stirred and the reaction was continued at 30° C. for 30 minutes. Using a Sephadex G25 column (1.5 cm diameter×30 cm) equilibrated with 0.1 mol/L phosphate buffer (pH 6.0), the reacted solution was subjected to gel filtration to remove unreacted EMCS, and maleimidated POD was collected.

The above-obtained solution of sulfhydrylated anti-MxA protein antibody KM1124 was mixed with the solution of maleimidated POD, and allowed to react at 30° C. for one hour. The obtained labeled antibody was diluted 800 times with a POD label diluent (liquid composition) buffer [50 mmol/L Bis-Tris (manufactured by DOJINDO Laboratories), 0.1% BSA (manufactured by InterGen)].

[5] Preparation of Sample Diluents

Sample diluents of the following compositions were prepared individually.

| | |
|---|---|
| HEPES (pH 8.0) | 0.1 mol/L |
| Surfactant | (type and concentration shown in Table 1) |
| NaCl | 1.5 mol/L |
| BSA | 0.1% |
| Sodium azide | 0.1% |

[6] Construction of an MxA Protein Assay System Using Sandwich ELISA

The MxA protein solution prepared in [2] mentioned above was diluted using the sample diluent prepared in [5] mentioned above to give the solutions of the MxA protein at the concentrations of 0 (buffer only), 3.2, 6.3, 12.5, 25, 50, 100, and 200 ng/mL, and these solutions were used as the samples for measurement.

To the anti-MxA protein antibody-immobilized plate produced in [3] mentioned above was added 100 µL of the samples for measurement, and then the mixture was incubated at room temperature for one hour to allow the MxA protein in the samples for measurement to bind to the antibody. After removing the samples for measurement, a washing operation of addition of 400 µL of washing solution (PBS containing 0.05% Tween 20 (manufactured by KANTO CHEMICAL)) followed by removal of the washing solution was performed five times. Next, 100 µL of the POD-labeled anti-MxA protein antibody solution prepared in [4] was added, and the reaction was continued at room temperature for 30 minutes. The labeled antibody was removed, and a washing operation of addition of 400 µL of washing solution and its removal was performed five times. In the dark, 100 µL of TMBlue (manufactured by Serological), which is a chromogenic substrate of POD containing 0.05% tetramethylbenzidine and hydrogen peroxide, was added and the reaction was continued at room temperature for ten minutes. The reaction was stopped by adding 100 μL of 0.5 mol/L sulfuric acid and incubating at room temperature for ten minutes. The absorbance at wavelength 450 nm was measured using a plate reader. The results showed that the absorbance increased as the concentration of MxA protein in the samples for measurement increased, and it proved that the MxA protein could be measured.

Actually, in case of the measurement of the concentration of MxA protein in the blood, a calibration curve obtained in this manner is used to determine the MxA protein in the blood.

[7] An Addition and Recovery Test of MxA Protein Using Blood

Blood collected from two MxA protein-positive patients found to have virus infection and from three healthy individuals using EDTA•2Na blood collection tubes was used.

Samples obtained by ten-fold dilution of this blood using the sample diluent of [5] were subjected to the measurement of the MxA protein concentration in each sample according to the method [6], and the determined concentrations were defined as the MxA protein concentration in a sample without added MxA protein (hereinafter, abbreviated as A).

Next, samples prepared by adding 1 part of the 500 ng/mL MxA protein solution prepared in [2] mentioned above to 9 parts of these sample solutions were subjected to the measurement of the MxA protein concentration in each sample according to the method [6], and the determined concentrations were defined as MxA protein concentration in MxA protein-added samples (hereinafter, abbreviated as B). The MxA protein recovery rates (%) was calculated from the equation below:

$$MxA \text{ Protein Recovery Rate } (\%)=(B-A)/50*100 \quad \text{(Equation 1)}$$

Theoretically, the MxA protein recovery rate (%) becomes 100% when an interference of hemoglobin is completely suppressed, and its value will decrease as the interference of hemoglobin appear.

COMPARATIVE EXAMPLE 1

The addition and recovery test was performed by a similar method to Example 1, except that a sample diluent lacking the surfactant from the composition of [5] in Example 1 was used as the sample diluent.

COMPARATIVE EXAMPLE 2

The addition and recovery test was performed by a similar method to Example 1, in which 0.2% Nonidet P40 was used as the surfactant in the composition of [5] in Example 1.

Table 1 shows that addition of a bile acid derivative in the measurements increases the level of MxA protein recovery rate, which indicates that an interference of hemoglobin is suppressed.

EXAMPLE 2

The sensitivity due to the addition of Nonidet P-40 to the sample diluent composition described in [5] above containing 4.9% CHAPS was examined. Nonidet P-40 was added to the sample diluent of [5] described above at 0%, 0.2%, 1%, and 1.4%, and solutions of the MxA protein prepared in the above-mentioned [2] were prepared at the concentrations of 0 (buffer only), 3.2, 6.3, 12.5, 25, 50, 100, and 200 ng/mL, and the absorbances (Abs) were measured by the method described in [6] in Example 1. The results are shown in Table 2.

TABLE 2

| MxA protein | Concentration of Nonidet P-40 added (%) | | | |
|---|---|---|---|---|
| (ng/mL) | 0.0 | 0.2 | 1.0 | 1.4 |
| 0 | 0.022 | 0.022 | 0.022 | 0.022 |
| 3 | 0.038 | 0.041 | 0.055 | 0.060 |
| 6 | 0.055 | 0.061 | 0.087 | 0.096 |
| 12 | 0.082 | 0.093 | 0.140 | 0.157 |
| 24 | 0.139 | 0.158 | 0.244 | 0.273 |
| 48 | 0.243 | 0.274 | 0.424 | 0.477 |
| 96 | 0.433 | 0.496 | 0.761 | 0.853 |
| 192 | 0.810 | 0.915 | 1.387 | 1.528 |

Table 2 shows that the absorbance increases to give an increased sensitivity, depending on the amount of Nonidet P-40.

EXAMPLE 3

Blood collected from two MxA protein-positive patients found to have virus infection and from three healthy individuals using EDTA•2Na blood collection tubes was used as samples.

The MxA protein recovery rate was determined in a similar manner as in Example 1, except that a sample diluent containing 4.9% CHAPS, a sample diluent containing 4.9% CHAPS and 1.4% Nonidet P-40 were used as the sample diluent. The results are shown in Table 3.

TABLE 1

| Surfactant | Concentration (%) | MxA protein recovery rate (%) | | | | | |
|---|---|---|---|---|---|---|---|
| | | Positive 1 | Positive 2 | Negative 1 | Negative 2 | Negative 3 | Average |
| CHAPS | 4.9 | 88.9 | 96.6 | 97.5 | 93.8 | 88.2 | 93.0 |
| CHAPSO | 5.0 | 76.3 | 92.1 | 100.0 | 91.4 | 86.9 | 89.3 |
| BIGCHAP | 2.5 | 76.7 | 91.8 | 103.3 | 86.6 | 88.2 | 89.3 |
| deoxy-BIGCHAP | 1.2 | 70.6 | 82.9 | 82.8 | 81.4 | 72.5 | 78.0 |
| Surfactant-free (Comparative Example 1) | 0 | 70.2 | 67.0 | 66.9 | 75.7 | 72.8 | 70.5 |
| Nonidet P-40 (Comparative Example 2) | 0.2 | 67.9 | 75.7 | 82.6 | 68.2 | 67.9 | 72.5 |

TABLE 3

| Surfactant | MxA protein recovery rate (%) | | | | | |
|---|---|---|---|---|---|---|
| | Positive 3 | Positive 4 | Negative 4 | Negative 5 | Negative 6 | Average |
| CHAPS | 93.9 | 89.3 | 96.1 | 97.5 | 98.3 | 95.0 |
| CHAPS + Nonidet P-40 | 90.1 | 83.8 | 96.1 | 100.5 | 104.2 | 94.9 |

Table 3 shows that the recovery rate does not decrease even when Nonidet P-40 is added.

INDUSTRIAL APPLICABILITY

The present invention provides a method of immunoassaying a component to be measured in a sample containing hemoglobin, which effects a suppression of an interference of hemoglobin and is useful for clinical diagnosis.

The invention claimed is:

1. A method of immunoassaying a component to be measured in a sample containing hemoglobin, which comprises:
   (i) reacting said component to be measured with an antibody capable of binding to the component in the presence of a bile acid derivative different from a bile acid derivative that is inherently contained in the sample to form an immune complex; and
   (ii) determining the amount of the component in the immune complex, wherein the component to be measured is a substance contained within cells or a protein induced within cells by cytokines wherein the bile acid derivative has amphoteric surfactant function or nonionic surfactant function.

2. The method according to claim 1, which comprises reacting said component to be measured in a sample containing hemoglobin with an antibody capable of binding to the component, further in the presence of a polyoxyethylene nonionic surfactant.

3. The method according to claim 1 or 2, wherein the method of immunoassay is a sandwich method or a competition method.

4. The method according to claim 1 or 2, wherein reacting the component with an antibody capable of binding to the component comprises:
   (1) reacting the component with a first antibody capable of binding to the component and a labeled second antibody capable of binding to the component,
   (2) reacting the component with a labeled competitive substance and an antibody capable of binding to both of the component and the competitive substance, or
   (3) reacting the component with a competitive substance and a labeled antibody capable of binding to both of the component and the competitive substance.

5. The method according to claim 1 or 2, wherein the bile acid derivative different from a bile acid derivative that is inherently contained in the sample is a bile acid derivative having amphoteric surfactant function.

6. The method of claim 1 or 2, wherein the bile acid derivative different from a bile acid derivative that is inherently contained in the sample is a bile acid derivative having nonionic surfactant function.

7. The method of claim 5, wherein the bile acid derivative having amphoteric surfactant function is 3-[(3-cholamidopropyl)dimethylammonio]propanesulfonate or 3-[(3-cholamidopropyl)dimethylammonio]-2-hydroxypropanesulfonate.

8. The method according to claim 6, wherein the bile acid derivative having nonionic surfactant function is N,N-bis(3-D-gluconamidopropyl)cholamide or N,N-bis(3-D-gluconamidopropyl)deoxycholamide.

9. The method according to claim 2, wherein the polyoxyethylene nonionic surfactant is polyoxyethylene alkylphenyl ether.

10. The method according to claim 1 or 2, wherein the sample is whole blood.

11. The method according to claim 1 or 2, wherein the component to be measured is MxA protein.

\* \* \* \* \*